United States Patent
D'Andrea et al.

(10) Patent No.: US 8,741,850 B2
(45) Date of Patent: Jun. 3, 2014

(54) COMPOUNDS MODULATORS OF VEGF ACTIVITY AND USES THEREOF

(75) Inventors: Luca Domenico D'Andrea, Naples (IT); Carlo Pedone, Naples (IT); Maria Caterina Turco, Avellino (IT)

(73) Assignee: Advanced Accelerator Applications S.A., St. Genis Pouilly (FR)

(*) Notice: Subject to any disclaimer, the term of this patent is extended or adjusted under 35 U.S.C. 154(b) by 0 days.

(21) Appl. No.: 13/386,506

(22) PCT Filed: Jul. 23, 2010

(86) PCT No.: PCT/EP2010/060722
§ 371 (c)(1),
(2), (4) Date: Jan. 23, 2012

(87) PCT Pub. No.: WO2011/009944
PCT Pub. Date: Jan. 27, 2011

(65) Prior Publication Data
US 2012/0114565 A1    May 10, 2012

Related U.S. Application Data

(60) Provisional application No. 61/228,384, filed on Jul. 24, 2009.

(51) Int. Cl.
| A61K 38/08 | (2006.01) |
| A61K 38/10 | (2006.01) |
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| A61K 38/16 | (2006.01) |

(52) U.S. Cl.
USPC ............................ 514/21.4; 530/326; 514/8.1

(58) Field of Classification Search
None
See application file for complete search history.

(56) References Cited

FOREIGN PATENT DOCUMENTS

WO    WO 0228895 A2 *   4/2002

OTHER PUBLICATIONS

Goncaleves et al "On-resin cyclization of a head-to-tail cyclopeptide using an allyldimethylsilyl polystyrene resin pre-loaded by metathesis" Tetrahedron 61:7789-7795. Published Aug. 8, 2005.*
Goncalves et al "On-resin cyclization of a head-to-tail cyclopeptide using an allyldimethylsilyl polystyrene resin pre-loaded by metathesis" Tetrahedron 61:7789-7795. Published online Jun. 15, 2006.*

* cited by examiner

*Primary Examiner* — Maury Audet
*Assistant Examiner* — Zachary J Miknis
(74) *Attorney, Agent, or Firm* — Snell & Wilmer LLP

(57) ABSTRACT

Compounds of general formula (1): $X_1Y_1X_2Y_2X_3Y_3X_4Y_4X_5X_5X_6Y_6X_7Y_7X_8X_9X_{10}$ wherein $X_1$-$X_{10}$ are any natural or unnatural amino acids and $Y_1$ is Gln; $Y_2$ is Met or Leu; $Y_3$ is Ile; $Y_4$ is Pro or Ser; $Y_5$ is His or Gly; $Y_6$ is Gln or Pro; $Y_7$ is Ile or Tyr or their homolog or ortolog are described; these compounds are able to bind to the VEGF receptors and to modulate the angiogenesis mediated by the VEG.

2 Claims, 4 Drawing Sheets

A)

B)

*p = 0.001477

SEQUENCE LISTING

```
<160> NUMBER OF SEQ ID NOS: 7

<210> SEQ ID NO 1
<211> LENGTH: 17
<212> TYPE: PRT
<213> ORGANISM: Artificial Sequence
<220> FEATURE:
<223> OTHER INFORMATION: prepared by chemical synthesis
<220> FEATURE:
<221> NAME/KEY: PEPTIDE
<222> LOCATION: (1)..(17)
<223> OTHER INFORMATION: linear

<400> SEQUENCE: 1

Lys Gln Ile Met Trp Ile Lys Pro His Gln Gly Gln Trp Ile Tyr Thr
1               5                   10                  15

Ser

<210> SEQ ID NO 2
<211> LENGTH: 17
<212> TYPE: PRT
<213> ORGANISM: Artificial Sequence
<220> FEATURE:
<223> OTHER INFORMATION: prepared by chemical synthesis
<220> FEATURE:
<221> NAME/KEY: PEPTIDE
<222> LOCATION: (1)..(17)
<223> OTHER INFORMATION: cyclic: Cys residues make a disulfide bond
<220> FEATURE:
<221> NAME/KEY: DISULFID
```

<222> LOCATION: (3)..(15)

<400> SEQUENCE: 2

Lys Gln Cys Met Trp Ile Lys Pro His Gln Gly Gln Trp Thr Cys Thr
1               5                   10                  15

Ser

<210> SEQ ID NO 3
<211> LENGTH: 17
<212> TYPE: PRT
<213> ORGANISM: Artificial Sequence
<220> FEATURE:
<223> OTHER INFORMATION: prepared by chemical synthesis
<220> FEATURE:
<221> NAME/KEY: PEPTIDE
<222> LOCATION: (1)..(17)
<223> OTHER INFORMATION: linear

<400> SEQUENCE: 3

Lys Gln Leu Leu Trp Ile Arg Ser Gly Asp Arg Pro Trp Tyr Tyr Thr
1               5                   10                  15

Ser

<210> SEQ ID NO 4
<211> LENGTH: 17
<212> TYPE: PRT
<213> ORGANISM: Artificial Sequence
<220> FEATURE:
<223> OTHER INFORMATION: prepared by chemical synthesis
<220> FEATURE:
<221> NAME/KEY: PEPTIDE
<222> LOCATION: (1)..(17)
<223> OTHER INFORMATION: cyclic: Cys residues make a disulfide bond
<220> FEATURE:
<221> NAME/KEY: DISULFID
<222> LOCATION: (3)..(15)

<400> SEQUENCE: 4

Lys Gln Cys Leu Trp Ile Arg Ser Gly Asp Arg Pro Trp Tyr Cys Thr
1               5                   10                  15

Ser

<210> SEQ ID NO 5
<211> LENGTH: 17
<212> TYPE: PRT
<213> ORGANISM: Artificial Sequence
<220> FEATURE:
<223> OTHER INFORMATION: PREPARED BY CHEMICAL SYNTHESIS
<220> FEATURE:
<221> NAME/KEY: PEPTIDE
<222> LOCATION: (1)..(17)
<223> OTHER INFORMATION: linear or cyclic
<220> FEATURE:
<221> NAME/KEY: VARIANT
<222> LOCATION: (1)..(1)
<223> OTHER INFORMATION: any natural or unnatural amino acid
<220> FEATURE:
<221> NAME/KEY: VARIANT
<222> LOCATION: (3)..(3)
<223> OTHER INFORMATION: any natural or unnatural amino acid
<220> FEATURE:
<221> NAME/KEY: VARIANT
<222> LOCATION: (4)..(4)
<223> OTHER INFORMATION: Met or Leu or their homolog or ortolog
<220> FEATURE:
<221> NAME/KEY: VARIANT
<222> LOCATION: (5)..(5)
<223> OTHER INFORMATION: any natural or unnatural amino acid
<220> FEATURE:
<221> NAME/KEY: VARIANT
<222> LOCATION: (7)..(7)

```
<223> OTHER INFORMATION: any natural or unnatural amino acid
<220> FEATURE:
<221> NAME/KEY: VARIANT
<222> LOCATION: (8)..(8)
<223> OTHER INFORMATION: Pro or Ser or their homolog or ortolog
<220> FEATURE:
<221> NAME/KEY: VARIANT
<222> LOCATION: (9)..(9)
<223> OTHER INFORMATION: His or Gly or their homolog or ortolog
<220> FEATURE:
<221> NAME/KEY: VARIANT
<222> LOCATION: (10)..(10)
<223> OTHER INFORMATION: any natural or unnatural amino acid
<220> FEATURE:
<221> NAME/KEY: VARIANT
<222> LOCATION: (11)..(11)
<223> OTHER INFORMATION: any natural or unnatural amino acid
<220> FEATURE:
<221> NAME/KEY: VARIANT
<222> LOCATION: (12)..(12)
<223> OTHER INFORMATION: Gln or Pro or their homolog or ortolog
<220> FEATURE:
<221> NAME/KEY: VARIANT
<222> LOCATION: (13)..(13)
<223> OTHER INFORMATION: any natural or unnatural amino acid
<220> FEATURE:
<221> NAME/KEY: VARIANT
<222> LOCATION: (14)..(14)
<223> OTHER INFORMATION: Ile or Tyr or their homolog or ortolog
<220> FEATURE:
<221> NAME/KEY: VARIANT
<222> LOCATION: (15)..(17)
<223> OTHER INFORMATION: any natural or unnatural amino acid

<400> SEQUENCE: 5

Xaa Gln Xaa Xaa Xaa Ile Xaa Xaa Xaa Xaa Xaa Xaa Xaa Xaa Xaa Xaa
1               5                   10                  15

Xaa

<210> SEQ ID NO 6
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: VEGF (UniProtKB/Swiss-Prot P15692) amino acid
      sequence 79-92
<300> PUBLICATION INFORMATION:
<308> DATABASE ACCESSION NUMBER: UniProtKB Swiss-Prot / P15692
<309> DATABASE ENTRY DATE: 1990-04-01
<313> RELEVANT RESIDUES IN SEQ ID NO: (79)..(92)

<400> SEQUENCE: 6

Gln Ile Met Arg Ile Lys Pro His Gln Gly Gln His Ile Gly
1               5                   10

<210> SEQ ID NO 7
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: PlGF (UniProtKB/Swiss-Prot P49763) sequence
      87-100
<300> PUBLICATION INFORMATION:
<308> DATABASE ACCESSION NUMBER: UniProtKB/Swiss-Prot P49763
```

```
<309> DATABASE ENTRY DATE: 1996-10-01
<313> RELEVANT RESIDUES IN SEQ ID NO: (87)..(100)

<400> SEQUENCE: 7

Gln Leu Leu Lys Ile Arg Ser Gly Asp Arg Pro Ser Tyr Val
1               5                   10
```

COMPOUNDS MODULATORS OF VEGF ACTIVITY AND USES THEREOF

CROSS REFERENCE TO RELATED APPLICATIONS

This application claims priority to International Application Number PCT/EP2010/060722 filed on Jul. 23, 2010 and U.S. Provisional Application No. 61/228,384 filed on Jul. 24, 2009, the entire contents of each of which are hereby incorporated by reference herein, in their entirety and for all purposes.

FIELD OF THE INVENTION

The present invention relates to compounds which interact with Vascular Endothelial Growth Factor (VEGF) receptors, modulate the VEGF dependent biological response and their use as pharmacological agents to treat angiogenesis-dependent diseases. These compounds mimic the β-hairpin region 79-92 of VEGF (or the corresponding fragment of Placenta Growth Factor) which is involved in receptors recognition. Here are described the design and biological properties of these compounds and their use for the treatments of pathologies dependent on the modulation of the VEGF biological activity, the diagnosis of pathologies which present a overexpression of VEGF receptors and as biochemical tools for the study of cellular pathway dependent on the activation of VEGF receptors.

REFERENCE TO A SEQUENCE LISTING

This application includes a Sequence Listing submitted electronically as a text file named 10541PTWO_seq listing_ST25.txt, created on Jul. 22, 2010, with a size of 4,000 bytes. The Sequence Listing is incorporated by reference herein.

STATE OF THE ART

Angiogenesis is a physiological process which refers to the remodeling of the vascular tissue characterized by the branching out of a new blood vessel from a pre-existing vessel. It is intimately associated with endothelial cell (EC) migration and proliferation. ECs are particularly active during embryonic development while during adult life EC turnover is very low and limited to particular physiological phenomena (Carmeliet, P. *Nat Med* 2003, 9, 653). In a healthy individual angiogenesis is finely tuned by pro- and anti-angiogenic factors, the shift from this equilibrium (angiogenic switch), under specific stimuli such as hypoxia, is related to several human diseases (pathological angiogenesis) (Hanahan, D., Folkman, *J. Cell* 1996, 86, 353). The prevalence of pro-angiogenic factors (excessive angiogenesis), is associate with cancer, proliferating retinopathy, rheumatoid arthritis and psoriasis. Whereas, insufficient angiogenesis is at the basis of coronary diseases, ischemia and a reduced capacity for tissue regeneration (Carmeliet, P., Jain, R. K. *Nature* 2000, 407, 249).

One of the most studied angiogenic factor is the Vascular Endothelial Growth Factor (VEGF). The VEGF and its receptors are overexpressed in pathological angiogenesis, making this system a target for therapeutic and diagnostic applications (Hanahan, D. et al. 1996 *Cell* 86, 353-364; Ferrara, N. et al. 1997 *Endocr Rev* 18, 4-25).

Vascular Endothelial Growth Factor

VEGF is a homodimeric glycoprotein, covalently bound by two disulfide bonds, characterized by a cystine knot motif. The vegf gene codify at least for eight splicing isoforms differing in the number of amino acids of the encoded polypeptide. The most common isoforms $VEGF_{121}$, $VEGF_{165}$, $VEGF_{189}$ and $VEGF_{206}$ are characterized by a different ability to bind to heparin, cell and matrices [148]. $VEGF_{121}$ is soluble and lack of the exons codifying for the heparin binding site; $VEGF_{165}$ is the most abundant form in the majority of tissues and in pathological angiogenesis, it binds to heparin and is found partially bound to the matrix; $VEGF_{189}$ and $VEGF_{206}$ strongly interact with matrix and are activated by proteolytic cleavage (Park et al., *Mol Biol Cell* 1993; 4: 1317-26; Roth et al. *Am J Pathol* 2006; 68: 670-84). An additional splice variant, $VEGF_{165b}$, has been identified and resulted an endogenous inhibitor of VEGF (Woolard et al., *Cancer Res* 2004; 64: 7822-35).

VEGF possess several homologs: VEGF-A, VEGF-B, VEGF-C, VEGF-D, PlGF and VEGF-E. They recognize different receptor and elicit diverse biological activity. VEGF-A (or VEGF) is the main form, it is a mitogen specific for vascular ECs and the main regulator of physiological and pathological angiogenesis. VEGF-B can form heterodimers with VEGF, it induces expression of enzymes involved in ECM degradation and EC migration, and it has a role in coronary artery development. VEGF-C and -D are mainly implicated in lymphagiogenesis; VEGF-C is mainly expressed during embryogenesis whereas VEGF-D is also expressed in adult heart, lung and skeletal muscle (Carmeliet P. *Nat Med* 2003; 9:653-60). VEGF-E is encoded by the parapoxvirus Orf virus. PlGF (Maglione et al., *Proc Natl Acad Sci USA* 1991; 88: 9267-71) is gaining much attention in the last years because of its role in pathological angiogenesis (Luttun et al., *Ann N Y Acad Sci* 2002; 979: 80-93; Fischer et al., *Cell* 2007; 131: 463-75; Luttun et al., *Nat Med* 2002; 8: 831-40). PlGF has been implicated in several physiological and pathological processes such as angiogenesis, arteriogenesis and atherosclerosis (Roy et al., *FEBS Lett* 2006; 580: 2879-87). It is mainly expressed in placenta and its expression is upregulated during pathological conditions such as ischemia and myocardial infarction (Iyer et al., *Trends Cardiovasc Med* 2002; 12: 128-34). PlGF loss does not affect embryonic development but impair angiogenesis during ischemia, wound healing, inflammation and cancer (Carmeliet et al., *Nat Med* 2001; 7: 575-83). Two main isoforms, PlGF-1 and PlGF-2, differing in the presence of high basic amino acids sequence and in the ability to bind to heparin have been described (Hauser S, Weich H A. *Growth Factors* 1993; 9: 259-68; Maglione et al., *Oncogene* 1993; 8: 925-31).

The biological activity of the VEGF family is mediated through the binding to three membrane receptors belonging to the tyrosine kinase family (VEGFR1, VEGFR2 and VEGFR3) and two receptors belonging to the semaphorin family (NRP1 and NRP2). The function of each receptor in physiological and pathological angiogenesis is still far to be completely revealed. A detailed description of the biology and pathologies associated to VEGF and its receptors can be found elsewhere (Nagy et al., *Annu Rev Pathol* 2007; 2: 251-75; Roy et al., *FEBS Lett* 2006; 580: 2879-87; Ferrara et al., *Nat Med* 2003; 9: 669-76; Ferrara N. *Curr Opin Biotechnol* 2000; 11: 617-24; Ferrara N, Davis-Smyth T. *Endocr Rev* 1997; 18: 4-25; Cross et al., *Trends Biochem Sci* 2003; 28: 488-94; Veikkola et al., *Cancer Res* 2000; 60: 203-12; Hicklin D J, Ellis L M. *J Clin Oncol* 2005; 23: 1011-27). VEGFR2 and VEGFR1 are mainly expressed on vascular endothelium but they have been found also on the surface of non-endothelial (Matsumoto T, Claesson-Welsh L. *Sci STKE* 2001; 2001: RE21) and tumor cells. Increased expression of these receptors occurs in response to several stimuli and results in priming of EC towards proliferation, migration and angiogenesis (Ferrara, N. et al. 2003 *Nat Med* 9, 669-676). They are composed of an intracellular kinase domain, a transmembrane region and an extracellular portion constituted of seven immunoglobulin-like domain. VEGF binds very tightly to both receptors but the binding affinity for VEGFR1 is ten times higher that for VEGFR2. They also differ in the ability to recognize VEGF homologs, in fact, VEGFR1 interacts also with PlGF and VEGF-B, whereas VEGFR2 recognizes VEGF-C, VEGF-D and VEGF-E. In a concise view of the receptors biology, the binding of VEGF induces receptor dimerization, autophosphorylation of the kinase domain and activation of several intracellular pathways ending with mitogenesis, angiogenesis, permeability, survival and migration. At embryonic stage VEGFR2 is essential for vasculogenesis and endothelial cells proliferations, while VEGFR1 is necessary for the organization of the vascular system of the embryo (Ferrara et al., *Nat Med* 2003; 9: 669-76). In the adult life VEGFR2 has been recognized as the mayor mediator of VEGF biological activity on ECs whereas VEGFR1 has been considered as a decoy receptor negatively regulating VEGF effects. Then, it has been showed that VEGFR1 is implicated in monocytes migration (Hiratsuka et al., *Proc Natl Acad Sci USA* 1998; 95: 9349-54), hematopoiesis (Hattori et al., *Nat Med* 2002; 8: 841-9) and in releasing tissue specific growth-factors (Ferrara et al., *Nat Med* 2003; 9: 669-76). Moreover, a cross-talk between the VEGF receptors, regulated by PlGF, was reported (Autiero et al. *Nat Med* 2003; 9: 936-43). An alternative splicing of VEGFR1 gene codifies for a receptor soluble form containing only six extracellular domain (sVEGFR1). This molecule binds to VEGF, suppresses VEGF mitogenic activity and acts as an efficient specific antagonist of VEGF in vivo (Kendall R L, Thomas K A. *Proc Natl Acad Sci USA* 1993; 90: 10705-9) Recently, it has been showed that sVEGFR1 has a role in pre-eclampsia (Maynard et al., *J Clin Invest* 2003; 111: 649-58).

VEGFR3 is found on the surface of lymphatic endothelial cells. It selectively binds to VEGF-C and VEGF-D and mediates lymphagiogenesis (Oliver G, Alitalo K. *Annu Rev Cell Dev Biol* 2005; 21: 457-83; Alitalo et al., *Nature* 2005; 438: 946-53). VEGFR3 is believed to play diverse roles assisting cardiovascular development, remodeling of primary vascular network during embryogenesis and facilitating lymphagiogenesis in adulthood [166]. Its activation has also been observed in some neoplastic conditions (Achen et al., *J Pathol* 2001; 193: 147-54; Valtola et al., *Am J Pathol* 1999; 154: 1381-90).

NRP1 and NRP2, mainly implicated in axonal guidance and neuronal development, are also involved in physiological and pathological angiogenesis, in fact, they act as co-receptor for VEGF. They do not transfer directly the intracellular signaling but enhance the binding affinity of the VEGF family members to VEGFR1 or VEGFR2. NRP1 binds to $VEGF_{165}$ and PlGF-2 and it is essential for neuronal and cardiovascular development, whereas NRP2 interact with $VEGF_{165}$ and VEGF-C and has a role in lymphagiogenesis (Pellet-Many et al., *Biochem J* 2008; 411: 211-26; Geretti et al., *Angiogenesis* 2008; 11: 31-9).

Structural Data of VEGF Family

Many structural data of VEGF family members have been reported. Several VEGF or PlGF structures have been described either free (Muller, Y A et al., *Structure* 1997, 5, 1325; Muller, Y. A. et al., *Proc Natl Acad Sci USA* 1997, 94, 7192), bound to peptide inhibitors (Wiesmann, C. et al., *Biochemistry* 1998, 37, 17765; Pan, B. et al., *J Mol Biol* 2002, 316, 769) or to a neutralizing antibody (Muller, Y A. et al., *Structure* 1998, 6, 1153). The only structural data about VEGFR1 regards the domain 2 of the extracellular region, $VEGFR1_{D2}$, in the free form (Starovasnik et al., *J Mol Biol* 1999; 293: 531-44), bound to VEGF (Wiesmann, C. et al., *Cell* 1997, 91, 695) or PlGF (Christinger et al., *J Biol Chem* 2004; 279: 10382-8). So far, no structural data have been reported for VEGFR3 and the extracellular domain of VEGFR2. Instead, VEGFR2 intracellular kinase domain has been described (McTigue et al., *Structure* 1999; 7: 319-30). A partial characterization of NRP1 and NRP2 receptors has been performed (Pellet-Many et al., *Biochem J* 2008; 411: 211-26). Very recently the complex between VEGF and the extracellular VEGFR1 domain has been observed by electron microscopy (Ruch et al., *Nat Struct Mol Biol* 2007; 14: 249-50). VEGF is an antiparallel homodimer, covalently linked through two disulfide bonds. It is characterized by a cystine knot motif. The knot consists of two disulfide bridges, with a third disulfide bond passing through them. The structure of the ligands and of the receptor does not change moving from the free forms to the complexed ones. Domain deletion studies on VEGFR1 and VEGFR2 showed that the ligand binding site resides within the first three extracellular domains and $VEGFR1_{D2}$ binds VEGF about 60-times less tight than wild type protein, but its removal completely abolishes the binding. The overall structure of the $VEGF/VEGFR1_{D2}$ complex possesses approximately a two-fold symmetry. The VEGF recognition interface is divided about 65% and 35% between both monomers. The analysis of structural and mutagenesis data allowed to identify residues involved in the binding to the receptors. They are distributed over a discontinuous surface which include residues from the N-terminal helix (17-25), the loop connecting strand 133 to 134 (61-66) and strand 137 (103-106) of one monomer, as well as residues from strand 132 (46-48) and from strand 135 and 136 together with the connecting turn (79-91) of the other monomer. The recognition interface is manly hydrophobic, except for the polar interaction between Arg224 (VEGFR1) and Asp63 (VEGF). VEGFR2 and VEGFR1 share the same VEGF binding region, in fact 5 out of 7 most important VEGF binding residues are present in both interfaces (Muller, Y. A. et al., *Proc Natl Acad Sci USA* 1997, 94, 7192; Wiesmann, C. et al., *Cell* 1997, 91, 695; Keyt et al., *J Biol Chem* 1996; 271: 5638-46).

NRPs receptors are transmembrane glycoproteins composed of an extracellular region constituted of two CUB domain (a1 and a2), two Factor V/VIII (b1 and b2) homology domain and a MAM domain, intracellularly they present a PDZ domain. The structures of domains a2, b1 and b2 of NRP1/2 in the free form (Lee et al., *Structure* 2003; 11: 99-108; Appleton et al., *Embo J* 2007; 26: 4902-12; Vander Kooi et al., *Proc Natl Acad Sci USA* 2007; 104: 6152-7), complexed to tuftsin (Vander Kooi et al., *Proc Natl Acad Sci USA* 2007; 104: 6152-7) and to an antibody (Appleton et al., *Embo J* 2007; 26: 4902-12) have been reported.

VEGF and Pathological Angiogenesis

The role of VEGF in different pathologies has been reported and blocking the interaction of VEGF with its receptors has been demonstrated to have several therapeutic applications. Many reviews and patents describe the role and the usage of VEGF inhibitors in pathological angiogenesis and discuss their therapeutic applications. All patent applications, patents and publications cited are hereby incorporated by reference in their entirety A diseases which can benefit from a therapy based on the inhibition of the interaction between VEGF and its receptors is cancer (D. J. Hicklin & L. M. Ellis *J. Clin. Onc.* 2005, 23, 1011; N. Ferrara et al., *Nat. Med.* 2003, 9, 669; N. Ferrara & T. Davis-Smyth *Endocr. Rev.* 1997, 18, 4). VEGF is overexpressed in several type of tumors (lung, thyroid, breast, gastrointestinal, kidney, ovary, uterine cervix, carcinomas, angiosarcomas, germ cell tumors, intracranial). VEGF receptors are overexpressed in some type of tumors, such as, non-small-cell lung carcinoma, melanoma, prostate carcinoma, leukemia, mesothelioma, breast carcinoma (D. J. Hicklin & L. M. Ellis *J. Clin. Onc.* 2005, 23, 1011), and on the surface on angiogenically active endothelial cells.

VEGF is implicated in intraocular neovascularization which may lead to vitreous hemorrhage, retinal detachment, neovascular glaucoma (N. Ferrara et al., *Nat. Med.* 2003, 9, 669; N. Ferrara *Curr. Opin. Biotech.* 2000, 11, 617) and in eye disorders such as age related macular degeneration and diabetic retinopathy (US 2006/0030529).

VEGF is also implicated in the pathology of female reproductive tract, such as ovarian hyperstimulation syndrome and endometriosis.

VEGF has been implicated in psoriasis, rheumatoid arthritis (P. C. Taylor *Arthritis Res* 2002, 4, S99) and in the development of brain edema.

Diseases caused by a defective angiogenesis can be treated (therapeutic angiogenesis) with agents able to promote the growth of new collateral vessels. The VEGF-induced angiogenesis has several therapeutic applications. Of course, molecules which bind to VEGF receptors and mimic the biological activity of VEGF are useful for the treatment of these diseases.

VEGF has been used for the treatments of ischemic cardiovascular diseases to stimulate the revascularization in ischemic regions, to increase coronary blood flow and to prevent restenosis after angioplasty. (M. Simons & J. A. Ware *Nat. Rev. Drug Disc.* 2003, 2, 1; N. Ferrara & T. Davis-Smyth *Endocr. Rev.* 1997, 18, 4).

VEGF and its receptors have been implicated in stroke, spinal cord ischemia, ischemic and diabetic neuropathy. VEGF is a therapeutic agent for the treatment of neuron disorders such as Alzheimer disease, Parkinson's disease, Huntington disease, chronic ischemic brain disease, amyotrophic later sclerosis, amyotrophic later sclerosis-like disease and other degenerative neuron, in particular motor neuron, disorders (US 2003/0105018; E. Storkebaum & P. Carmeliet *J. Clin. Invest.* 2004, 113, 14).

VEGF has a basic role in bone angiogenesis and endochondral bone formation. These findings suggest that VEGF may be useful to promote bone formation enhancing revascularization. Conditions which can benefit from a treatment with VEGF are bone repair in a fractures, vertebral body or disc injury/destruction, spinal fusion, injured meniscus, avascular necrosis, cranio-facial repair/reconstruction, cartilage destruction/damage, osteoarthritis, osteosclerosis, osteoporosis, implant fixation, inheritable or acquired bone disorders or diseases (US2004/0033949).

VEGF has been implicated in the process of gastric ulcer (Ma et al., *Proc. Natl. Acd. Sci. USA* 2001, 98, 6470) wound healing, diabetic foot ulcers and diabetic neuropathy.

VEGF has been implicated in neurogenesis (K. Jin et al., *Proc. Natl. Acd. Sci. USA* 2002, 99, 11946) and for the treatment of pathological and natural states benefiting from the formation or regeneration of new vessels (US 2005/0075288)

VEGF or molecules able to bind to VEGF receptors can be useful for the diagnosis of pathologies which present a over-expression of VEGF receptors (Li et al., *Annals of Oncology* 2003, 14, 1274) and to imaging angiogenic vasculature (Miller et al., *J. Natl. Cancer Inst.* 2005, 97, 172).

Molecular agents for imaging angiogenesis must bind to the VEGF receptors with high specificity and be detectable at low concentrations. They should be labeled according to the imaging modalities, PET, SPECT, and, to a lesser extent, ultrasound (with microbubble contrast agents) and optical imaging (with fluorescent contrast agents). In addition, even though the sensitivity of MRI is low, molecular imaging of angiogenesis is possible with oligomerized paramagnetic substances linked to an agent, that binds a molecular marker of angiogenesis (Miller et al., *J. Natl. Cancer Inst.* 2005, 97, 172).

Therefore, there is the need to develop compounds able to modulate VEGF-dependent diseases as therapeutic, diagnostic or imaging agents.

This invention relates to synthetic peptides designed to mimic the VEGF β-hairpin region 79-92 (or 87-100 of PlGF) able to bind to the VEGF receptors and to modulate the angiogenesis mediated by the VEGF.

The compounds described in the present invention promote or inhibit the angiogenesis process and have application in the pro- or anti-angiogenesis therapy. Moreover, they are useful as diagnostic agents, for example in the imaging of tumor or endothelial cells overexpressing the VEGF receptors. Finally, they have application as biochemical tools for the study of cellular pathway dependent on the activation of VEGF receptors.

These compounds have been designed starting from the molecular structure of the complex VEGF-VEGFR1-D2 (Wiesmann, C. et al., *Cell* 1997, 91, 695; *Protein Data Bank code 1FLT*). The VEGF (UniProtKB/Swiss-Prot P15692) amino acid sequence 79-92 (QIMRIKPHQGQHIG; one-letter amino acid code; SEQ ID No: 6), comprising strands β5 and β6, adopts a β-hairpin conformation both in the VEGF free and complexed form. Mutagenesis experiments showed that residues Gln79, Ile83, Lys84 and Pro85 are important for VEGFR2 recognition. From the structural analysis of the complex VEGF-VEGFR1-D2 the authors identified the VEGF residues (Gln79, Met81, Ile83, Pro85, His86, Gln89, Ile91) situated at less than 4.5 Å from the receptor. A corresponding analysis on the PlGF (UniProtKB/Swiss-Prot P49763; sequence 87-100: QLLKIRSGDRPSYV; SEQ ID No: 7) highlighted the residues Gln87, Leu89, Ile91, Pro97 and Tyr99.

The design strategy consisted in keeping fixed the tridimensional arrangement of the interacting residues constraining the amino acid sequence 79-92 to adopt a molecular conformation like the natural one. To stabilize the beta-hairpin structure and considering that turn residue cannot be modified because they are involved in the binding to the receptor, the authors decided to introduce in the amino acid sequence, where possible, amino acids with high propensity for a beta conformation and stabilize the fold of the two strands using two molecular tools: hydrophobic cluster and disulfide bond. The first strategy consisted in introducing, in specific position across the two strands, hydrophobic amino acids, especially aromatic, in order to form a hydrophobic cluster which keep the two strand folded (Cochran et al., *Proc Natl Acad Sci USA*. 2001; 98: 5578-83). The latter strategy consisted in introducing two cysteine residues in order to form a disulfide bond between the two strands. Polar residue with high preference for a beta conformation, such as serine and threonine, were also introduced in order to stabilize the β-hairpin and improve water solubility. Finally, a lysine residue was appended in order to complete strand pairing and allow peptide derivatization.

SUMMARY OF THE INVENTION

It is therefore the object of the present invention a molecule of general formula (1) (SEQ ID No 5):

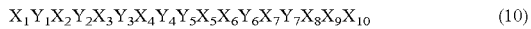  (10)

wherein

X1-X10 are any natural or unnatural amino acids and Y1 is Gln; Y2 is Met or Leu;

Y3 is Ile; Y4 is Pro or Ser; Y5 is His or Gly; Y6 is Gln or Pro; Y7 is Ile or Tyr or their homolog or ortolog.

Preferably X2, X3, X7 and X8 are amino acids that stabilize the structure of the molecule.

Still preferably X2, X3, X7 and X8 are selected from the group of: Cys, Trp, Tyr, Ile, Glu, Lys, Phe, Asp.

Yet preferably X4, X5 and X6 are residue present in the natural protein VEGF or PlGF such as Arg, Lys, Gln, Asp, Gly, Arg.

Preferably X9 and X10 are Ser and Thr, respectively.

Preferably the molecule is selected from the group of: KQIMWIKPHQGQWIYTS (SEQ ID No 1); KQCMWIKPHQGQWTCTS (SEQ ID No 2); KQLLWIRSGDRPWYYTS (SEQ ID No 3); KQCLWIRSGDRPWYCTS (SEQ ID No 4).

Preferably, the molecule of the invention is for medical use, in particular for use of a VEGF-dependent pathology.

Preferably the pathology is selected from the group of: cancer, eye disorders, pathology of female reproductive tract, psoriasis, rheumatoid arthritis, brain edema, diseases caused by defective or excessive angiogenesis, ischemic cardiovascular diseases, brain disorders, bone pathology, osteoarthiritis, osteosclerosis, esteoporosis.

It is a further object of the invention the use of the molecule of the invention for the diagnosis of a VEGF-dependent pathology.

It is further object of the invention the use of the molecule of the invention as an imaging agent. Preferably the molecule is labelled.

Still preferably the label is a contrast or a paramagnetic agent.

Preferably angiogenic vasculature is imaged.

It is further object of the invention a pharmaceutical composition comprising the molecule of the invention as described above and appropriate diluents and/or excipients.

In the general formula (1) (SEQ ID No 5):

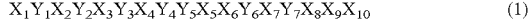  (1)

X residue are important for the conformational stabilization of the molecule while Y residues are interacting residues.

X1-X10 are any natural or unnatural amino acids, including D-amino acids: Ala, Arg, Asn, Asp, Cys, Gln, Glu, Gly, His, Ile, Leu, Lys, Met, Phe, Pro, Ser, Thr, Trp, Tyr, Val, α-amino-glycine, α,β-diaminopropionic acid, ornitine, 2,6-diamino-4-hexynoic acid, 4,5-dehydro-lysine, ω-hidroxy-norarginine, α,γ-diaminobutyric acid, α-difluoromethyl-ornitine, 4-amino-piperidine-4carboxylic acid, d-hydroxy-lysine, homoarginine, dehydroalanine, β-cyclopropil-alanine, β-(1-cyclopentenyl)-alanine, β-cyclohexyl-alanine, penicilamine, β-fluoro-alanine, tert-butyl-alanine, β-cyclopentenyl-alanine, β,β-dicyclohexyl-alanine, 4,5-dehydro-leucine, β-chloro-alanine, propargyl-glicine, thioproline, 4-fluoro-proline, allo-isoleucine, azetidine-2-carboxylic acid, 2-allyl-glycine, 3,4 dehydro-proline, α-methyl-proline, pipecolinic acid, α-aminobutyric acid, tert-butyl-glicine, α-methyl-valine, norvaline, cyclohexil-glicine, β-cyano-alanine, allo-threonine, hydroxy-proline, 6-diazo-5-oxo-norleucine, β-(2-thiazolyl)-alanine, α-amino-isobutyric acid, β-ureido-alanine, citrulline, homocitrulline, β-(1,2,4-triazol-1-yl)-alanine, homocysteine, pyroglutamic acid, thiocitrulline, S-methyl-thiocitrulline, β-(2-thienyl)-serine, γ-hydroxy-glutamic acid, γ-methylene-glutamic acid, γ-carboxy-glutamic acid, α-aminoadipic acid, 2-aminoheptanedioic acid, α-aminosuberic acid, ω-amino-arginine, α-methyl-histidine, 1-methyl-histidine, β-(2-pyridyl)-alanine, β-(2-Quinolyl)-alanine, ω-methyl arginine, 2,5-diiodo-histidine, 3-methyl-histidine, β-(3-pyridyl)-alanine, 3-amino, tyrosine, 1-amino-cyclopentanecarboxilic acid, β-(2-thienyl)-alanine, 1,2,3,4-tetrahydroisoquinoline-3-carboxylic acid, spinacine, 4-amino-phenylalanine, α-methyl-leucine, β-(3-benzothienyl)-alanine, β-(1-naphtyl)-alanine, β-(2-naphthyl)-alanine, β,β-diphenyl-alanine, norleucine, phenilglycine, 4-iodo-phenilalanine, 3,4-dichloro-phenylalanine, 4-methyl-phenylalanine, octahydrohyndole-2-carboxylic acid, 4-bromo-phenylalanine, 3-fluoro-phenilalanine, 4-chloro-phenilalanine, 4-phenyl-phenylalanine, α-methyl-phenylalanine, homophenilalanine, 4-tert-butyl-phenylalanine, 4-fluoro-phenilalanine, 2,3,4,5,6-pentafluoro-phenylalanine, 2-mercapto-histidine, 4-azido-phenylalanine, α-methyl-tryptophan, 4-methyl-tryptophan, 4-benzoyl-phenylalanine, 4-nitro-phenylalanine, 4-cyano-phenylalanine, 3-iodo-tyrosine, 5-methyl-tryptophan, 1,2,3,4-tetrahydronorharman-3-carboxylic acid, β-(3,4-diihydroxy-phenyl)-serine, 3,5-dinitro-tyrosine, 3-nitro-tyrosine, 7-hydroxy-1,2,3,4-tetrahydroiso-quinoline-3-carboxy acid, 3-hydroxylmethyl-4-isopropylidene-tyrosine, 4-carboxy-phenylalanine, 3,5-dibromo-tyrosine, 3,5-diiodo-tyrosine, thyronine, aminohexanoic acid, aminoserine, butylglicine, dihydroxyphenilalanine, homoserine, isonipecotic acid, sarcosine, Y1 is Gln;
Y2 is Met or Leu;
Y3 is Ile;
Y4 is Pro or Ser;
Y5 is His or Gly;
Y6 is Gln or Pro;
Y7 is Be or Tyr Preferably positions Y1 to Y7 correspond, but are not limited, to human VEGF residues Gln79, Met81, Ile83, Pro85, His86, Gln89, Ile91, human PlGF residues Gln 87, Leu89, Ile91, Ser93, Gly94, Pro97 and Tyr99 or a their combination. Obviously, the Y residues could also be derived by any combination of residues belonging to a VEGF homolog (VEGF-B/UniProtKB/Swiss-Prot P49765, VEGF-C/UniProtKB/Swiss-Prot P49767, VEGF-D/UniProtKB/Swiss-Prot O43915) or ortholog.

Preferably in positions X2, X3, X7 and X8 are inserted amino acid in order to conformational stabilize the β-hairpin structure by means of covalent bond or non covalent interactions, for example residues X2, X3, X7 and X8 could be any of the following: Cys, Trp, Tyr, Ile, Glu, Lys, Phe, Asp. X4, X5 and X6 preferably are residue present in the natural protein VEGF or PlGF such as Arg, Lys, Gln, Asp, Gly, Arg. Preferred amino acid in position X9 and X10 are those with a high preference for a beta conformation (Smith et al., *Biochemistry* 1994, 33, 5510; Minor L. & Kim P S *Nature* 1994, 367, 660): Ile, Met, Phe, Ser, Thr, Trp, Tyr, Val, preferably Ser and Thr.

Preferred peptide sequences are:

```
                                                    (SEQ ID No 1)
#1    KQIMWIKPHQGQWIYTS (linear)
```

-continued

```
#2    KQCMWIKPHQGQWTCTS (cyclic: Cys residues    (SEQ ID No 2)
      make a disulfide bond)

#3    KQLLWIRSGDRPWYYTS (linear)                 (SEQ ID No 3)

#4    KQCLWIRSGDRPWYCTS (cyclic: Cys residues    (SEQ ID No 4)
      make a disulfide bond)
```

The present invention comprises also derivatives of the general molecule (1) or peptides #1-#4 as their cyclic analogs where cyclization could interest the backbone, backbone and side chain or side chain-side chain. Other analogs derive by introduction (or replacement) of a covalent bond across two residues belonging to the two strands. The cyclization linkage could be, but are not limited to: lactam bond, carbon-carbon bond, thioether bond, ether bond, an oxime linker, a lanthionine linker, diaryl ether or diarylamine linkage, thiazolidine linkage or as result of reaction such as click chemistry (Angell Y L, Burgess K. *Chem Soc Rev.* 2007; 36: 1674-89), Staudinger ligation (Nilsson et al., *Org Lett.* 2000; 2: 1939-41; Saxon et al., *Org Lett.* 2000; 2: 2141-3), chemical ligation (Dawson and Kent *Annu Rev Biochem.* 2000; 69: 923-60), Olefin Metathesis (Schuster et al, *Angewandte. Chem. Int. Edn Engl,* 36:2036-2056 (1997)).

The β-harpin structure could also been stabilized by introducing organic β-turn mimetic or inducer to chemically connect the peptide N- and C-termini.

The present invention comprises also other derivatives in which one or more amino acid side chains are protected with a protecting group, peptide N- and C-termini are free, capped with acetyl, amide, ester, thioester, acyl, alkyl, carboxyl, amine, ect. groups, or present additions or truncations in the N- and/or C-termini.

It is also within the scope of the invention the modification or optimization of the described peptides in order to increase their potency, pharmacokinetic behavior, stability and/or other biological, physical and chemical properties.

Possible modification, for example, are:

Substitution of the backbone amide bonds with the insertion of alpha-N-methylamides, thioamides, amines, semicarbazone derivatives, olefin bond; substitution of L-amino acid with a D-amino acid, substitution of alkyl-substituted hydrophobic amino acids with an aliphatic side chain from C1-10 carbons including branched, cyclic and straight chain alkyl, alkenyl or alkynyl substitutions; substitution of aromatic amino acids; substitution of amino acids containing basic functions; substitution of acidic amino acids; substitution of side chain amide residues, substitution of hydroxyl containing amino acids;

Are also in the scope of the present patent application a retroinverse peptide, a peptoid, multimeric constructs of the described sequences. In addition, are also included derivatives of the described sequences which functionalized with a chemical entity such as, but not limited to, glycosyl, PEG, lipid, a metal chelating unit, a fluorescent probe, biotin-derivatives.

Biological and in vivo assays showed that molecules based on the general formula (1) are able to bind to VEGF receptors and modulate the angiogenic response. The authors found that the compound #3 (KQLLWIRSGDRPWYYTS) has a proangiogenic biological activity whereas compounds #1, #2 and #4 showed an antiangiogenic activity. The compounds have application in diagnosis and treatment of pathologies depending on angiogenesis, especially they can be used in therapy of angiogenesis.

The compounds have applications in diagnosis and treatment of pathological states depending on excessive angiogenesis, of pathological and natural states benefiting from the formation or regeneration of new vessels, of pathologies which present a overxpression of VEGF receptors.

BRIEF DESCRIPTION OF THE FIGURES

The invention will be now described by non limiting examples referring to the following figures.

DETAILED DESCRIPTION OF THE INVENTION

Figure 1:
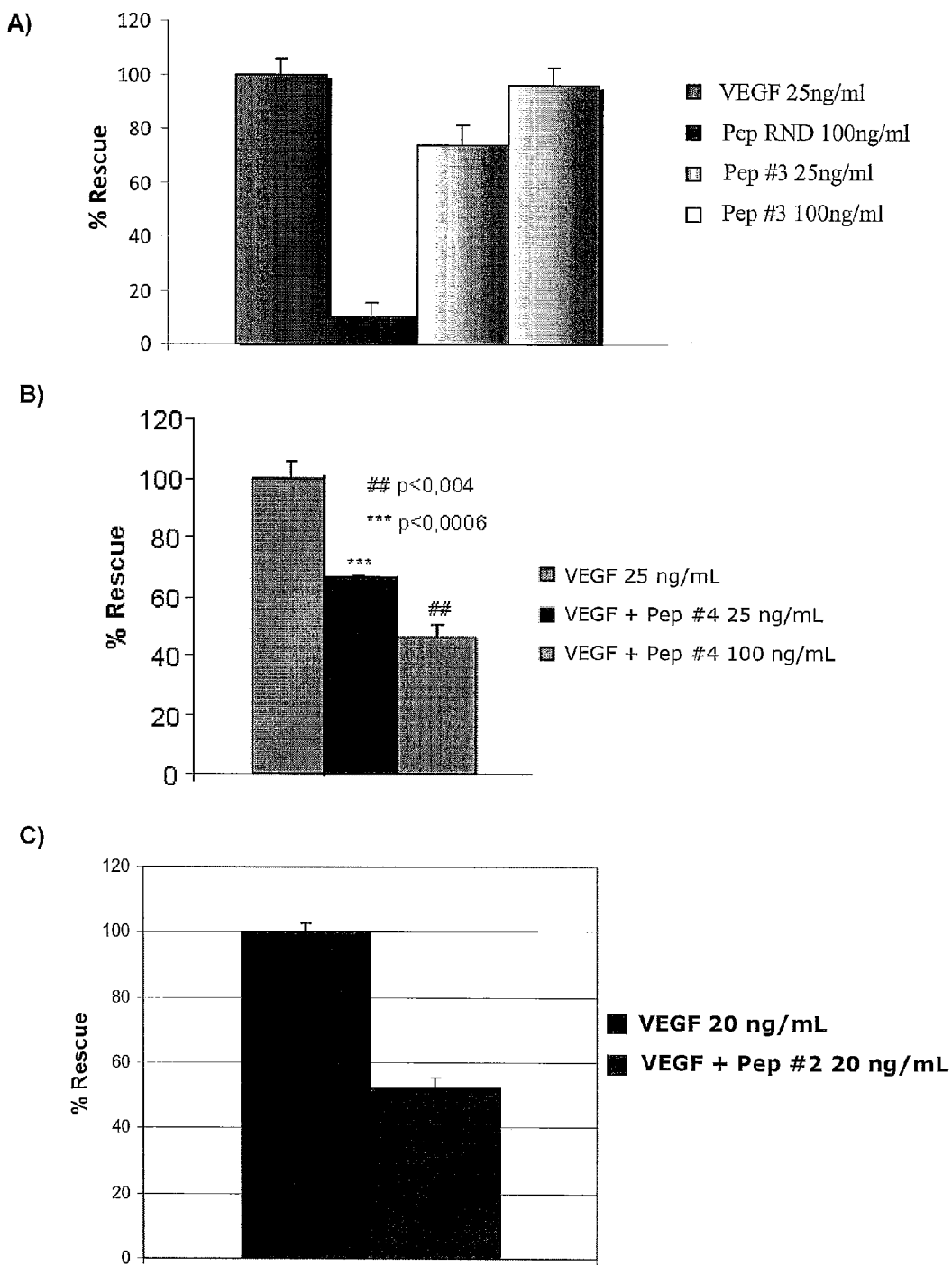
FIG. 1—HUVE cells ($1 \times 10^4/cm^2$) were incubated in starvation medium (EBM-2, 0.1% heparin, 0.1% BSA) with A) peptide #3 (25-100 ng/ml) or scrambled peptide pep-RND (100 ng/ml); B) peptide #4 or C) peptide #2 at 37° C. in 5% $CO_2$ atmosphere. VEGF165 was used as positive control (see methods). After 8 hours, caspase-3 activity was determined. Data are reported as percent of cell rescue from caspase-3 activation with respect to control.

Material and Methods
Peptide Synthesis

Peptides were synthesized on solid phase using Wang resin (Novabiochem) with standard Fmoc (N-(9-Fluorenyl)methoxycarbonyl) chemistry. The N-terminal lysine was protected with the methyltrytil group to allow selective deprotection and peptide labeling. Cleavage from the resin were achieved by treatment with trifluoracetic acid, triisopropyl silane, water, etanedithiol (93; 2, 2.5; 2.5) at room temperature for 3 hours. Purity and identity of the peptides were assessed by HPLC and MALDI-ToF mass spectrometry. The VEGF used as positive control was the commercial available $VEGF_{165}$ (UniProtKB/Swiss-Prot P15692-4)

Cell Culture

HUVEC (Human Umbilical Vein Endothelial Cells) were purchased from Promocell (Heidelberg, Germany). All experiments were performed on low passage cell cultures. Cells were grown in EGM-2 (Endothelial Growth medium) (EBM-2, FBS 2%, VEGF, R3-IGF-1, hEGF, hFGF, hydrocortisone, ascorbic acid, heparin and GA-1000) (Clonetics, Cambrex Bio Science Walkersville, Inc., Walkersville Md. USA) at 37° C. and in 5% CO2.

Caspase 3 Fluorimetric Assay

Determination of caspase-3 activity was performed by a fluorometric assay based on the proteolytic cleavage of the AMC-derived substrate N-acetil-DEVD-AMC, which yields a fluorescent product.

HUVEC cells were plated in 6-well dishes at $1 \times 10^5$ cells/$cm^2$. On the next day, cells were treated, in starvation medium (EBM-2, heparin 0.1%, BSA 0.1%), with Pep #3 (25-100 ng/ml) or scrambled Pep RND (100 ng/ml) peptides for 8 h at 37° C. VEGF165 (R & D Systems, Minneapolis, Minn., USA), 25 ng/ml, was used as positive control.

After 8 h the cells were processed with 150 µl of Caspase-3 reaction buffer (HEPES pH 7.5 50 mM, EDTA 0.1 mM, NP-40 0.1%, CHAPS 0.1%, DTT 1 mM) and cell proteins collected after centrifugation at 13000 rpm for 15 min at 4° C. Protein concentrations were determined by Bradford method (Bio-Rad, Hercules, Calif.) and 20 µg of lysates were incubated in 96-well plates with 20 µM N-acetil-DEVD-AMC at 37° C. for 3 h.

Samples were analyzed using a microplate reader (L55 Luminescence Spectometer Perkin Elmer Instruments) (excitation: 360 nm, emission: 440 nm).

Western Blot

Cells were plated in 12-well dishes at $1 \times 10^5$ cells/$cm^2$. On the next day, cells were treated, in starvation medium (EBM-2, heparin 0.1%, BSA 0.1%) with Pep #3 (25-100 ng/ml) or Pep RND (100 ng/ml) peptides for 15 min and 30 min at 37° C. VEGF165 (R & D Systems, Minneapolis, Minn., USA) 25 ng/ml was used as positive control. After treatment, whole cell lysates were obtained by using RIPA lysis buffer (Tris 50 mM pH 7.5, NaCl 150 mM, NP-40 1%, EGTA 1 mM, SDS 0.05%) supplemented with Complete Protease Inhibitors and Phosphate Inhibitors (Pierce Biotechnology, Rockford, Ill.). Cell proteins were then collected after centrifugation and protein content was determined by Bradford method (Bio-Rad, Hercules, Calif.). Proteins were separated by electrophoresis on SDS-polyacrylamide gels and transferred to nitrocellulose membrane (Millipore Corp., Bedford, Mass.) by semi-dry electroblotting (Transblot; Bio-Rad Laboratories, Hercules, Calif.).

The serine-tyrosine-phosphorilated ERK1/2 (polyclonal antibody, Cell Signaling Technology, Inc. Danvers, Mass., USA) and αGAPDH (monoclonal antibody 6C5, Santa Cruz Biotechnology, Inc., Santa Cruz, Calif.) were visualized by specific antibodies, anti-rabbit and anti-mouse horseradish peroxidase-conjugated secondary antibody (Jackson Immunoresearch Laboratories, Inc, Baltimor Pike; Pa., USA) standard chemiluminescence (Pierce Biotechnology, Rockford, Ill.).

Cell Proliferation Assay

HUVEC cells were plated at density of 1200 cells/well in 96-well poly-D-lysine-coated microplates (Becton Dickinson, Franklin Lakes, N.J. USA). After 24 hours incubation in starvation medium (EBM-2, heparin 0.1%, BSA 0.1%), cells were treated with VEGF165 25 ng/ml (R & D Systems, Minneapolis, Minn., USA), with Pep #3 (10-25-50-100 ng/ml) or Pep RND (100 ng/ml). Cell proliferation was determined by using CyQUANT® NF Cell Proliferation Assay Kit (Molecular Probes, Invitrogen S.R.L., Milano, Italy) at 24, 48 and 72 hour after treatment. CyQUANT® NF assay is based on cellular DNA content measurement via fluorescent dye binding. Because cellular DNA content is highly regulated, it is closely proportional to cell number. Briefly, medium was removed and cells incubated with CyQUANT NF reagent for 1 hour at 37° C. according to the manufacturer's instructions. Plates were then analyzed by using a microplate reader (L55 Luminescence Spectometer Perkin Elmer Instruments) (excitation: 485 nm, emission: 520 nm).

Animals

Female CD1 mice (20-25 g) were supplied by Charles-River (Italy) and kept in temperature- and humidity-controlled rooms (22° C., 50%) with lights on from 07:00 to 19:00 h, water and food available ad libitum. All procedures were carried out in accordance with the Italian law (Legislative Decree no. 116, 27 Jan. 1992), which acknowledges the European Directive 86/609/EEC, and were fully compliant with GlaxoSmithKline policy on the care and use of laboratory animal and codes of practice. Furthermore, all efforts were made to minimize the number of animals used and their suffering.

Directed in Vivo Angiogenesis Angioreactor (DIVAA)

Sterile silicone cylinders closed at one end, called angioreactors (Cultrex, Trevigen, Inc. Helgerman Conn., Gaithersburg), were filled with 20 µL of basement membrane extract (BME) premixed with or without angiogenesis factors (VEGF, FGF) to obtain positive and negative controls respectively. Furthermore HPLW (100 ng/ml) or scrambled HW-RND (100 ng/ml) peptides were added to angioreactors. These were incubated at 37° C. for 1 hour to allow gel formation, before subcutaneous implantation into the dorsal flank of CD1. Animals were anaesthetized before implantation with 100 mg/ml Ketamine HCL and 20 mg/ml Xylazine injected subcutaneously. Incision were made on the dorsal flank (left and right) of mouse, approximately 1 cm above the hip-socket, and were closed with skin staple.

Vessel formation evaluation was performed after 21 days. Matrigel was removed from angioreactors and digested in 300 µl of CellSperse solution for 1 hour at 37° C. After digestion, the incubation mix was cleared by centrifugation at 800 rpm. Cell pellets were resuspended in 500 µl of DMEM 10% FBS and plated on coverslips in 24-wells plates for 16 hour at 37° C. in 5% CO2. Cells were fixed with a 3.7% formaldehyde solution for 30 min at room temperature and quenched by incubation with 0.1 mM glycine for 5 min. Subsequently, cells were incubated with FITC-Lectin reagent (available in the kit) and then observed by fluorescence microscope (ZEISS, German).

Results

Peptides Biological Effects on Caspase 3 Activity

To investigate the biological activity of the designed peptides the authors analyzed the activation of caspase 3 in human primary endothelial (HUVEC) cells serum-deprived by means of a caspase-3 fluorimetric assay. It is well known that VEGF act as survival factor for ECs. When serum starved caspase 3 activity increases, therefore, the addition of VEGF partially rescued, as expected (Yilmaz A, et al., *Biochem Biophys Res Commun.* 2003, 306: 730-6), HUVEC cells from apoptosis. Experiments were performed on serum starved HUVEC treated with designed peptides in presence or absence of VEGF in order to highlight an antagonist or agonist (VEGF-like) activity respectively. The biological activity of the analyzed compounds is reported as percentage of VEGF rescue (FIG. 1). The decrease of the caspase-3 activity following VEGF incubation is set to 100% rescue. Caspase-3 activity, measured after 8 hour, was significantly decreased (and consequently the rescue was significantly increased) by Peptide #3 at final concentrations of 25 ng/ml and 100 ng/ml, in respect to untreated cells and scrambled (Pep-RND)-treated cells.

The effect of VEGF was partially abolished when peptide #2 and #4 were added to the cultures (FIGS. 1B and 1C).

Biological Effects of Peptides #3 and #4 on ERK 1/2 and AKT Activation

Figure 2:
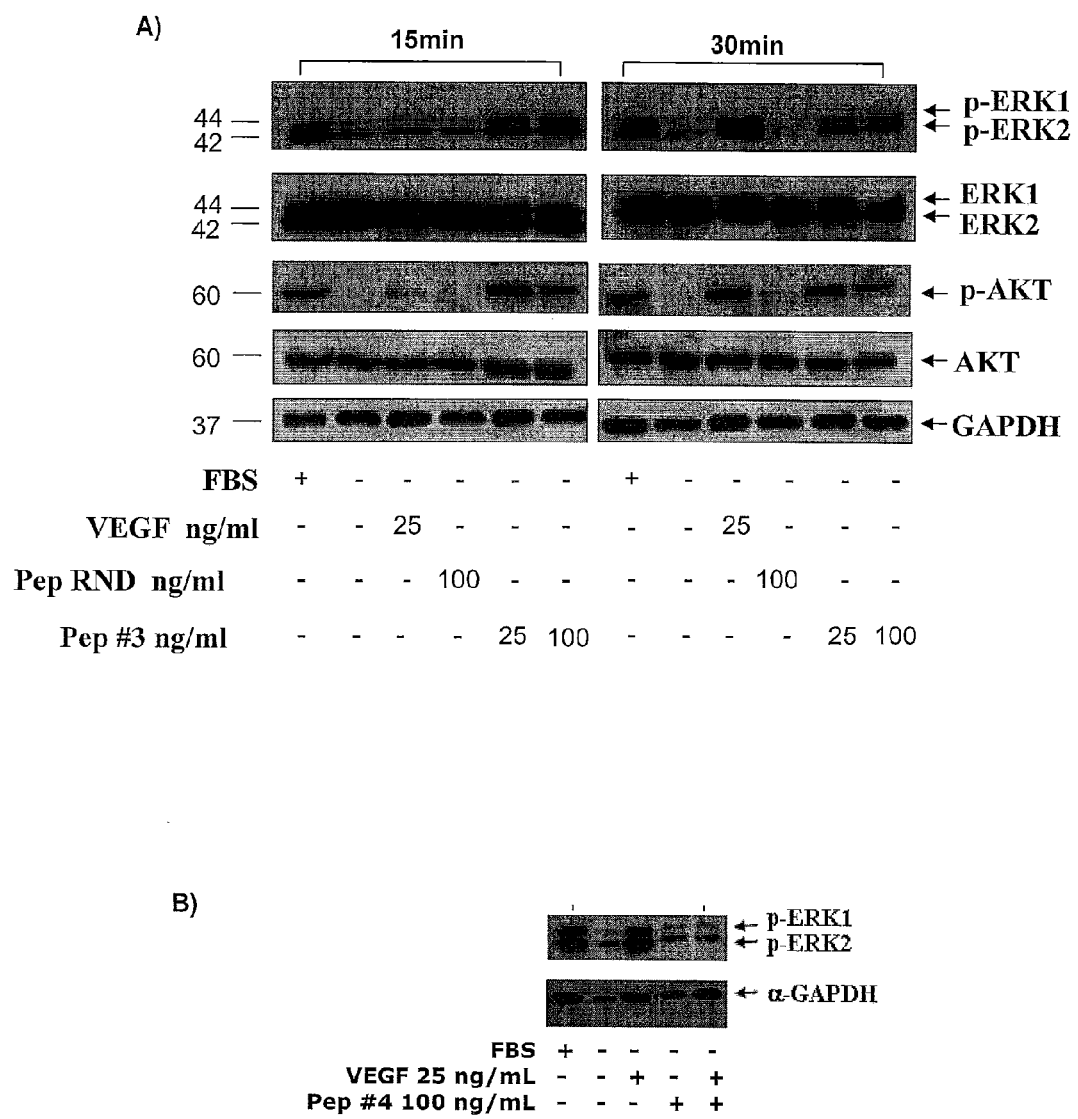
FIG. 2—HUVE cells were incubated in starvation medium (EBM-2, 0.1% heparin, 0.1% BSA) with VEGF (25 ng/ml) or A) peptide #3 (25-100 ng/ml), scrambled Pep-RND (100 ng/ml) peptides for 15 min and 30 min; B) in the absence or presence of peptide #4 (100 ng/ml) for 30 min. The experiment was performed at 37° C. in 5% $CO_2$ atmosphere. Proteins were analyzed for phospho ERK1/2 content by immunoblotting. An antibody recognizing GAPDH was used to monitor equal loading conditions.

VEGF-modulated angiogenesis is largely ERK1/2-dependent, leading to DNA synthesis and cell proliferation. VEGF binding to HUVEC cells was shown to induce the activation of ERK kinase. The authors therefore investigated whether peptide #3 could also induce ERK and AKT activation like VEGF. HUVEC cells, treated with peptide #3 (25-100 ng/ml) in serum deprivation conditions for 15 and 30 min, displayed ERK1/2 and AKT activation, as shown in western blot analyses by using an anti-phospho serine-tyrosine ERK1/2 and AKT antibodies (FIG. 2A). Scrambled Pep-RND had no effect on ERK1/2 and AKT activation, proving that it is unable to activate intracellular signaling (FIG. 2A).

Peptide #4, instead, at 100 ng/mL does not show any biological effect on untreated HUVE cells but dramatically reduces ERK 1/2 activation of VEGF stimulated HUVE cells, confirming its biological inhibitory activity (FIG. 2B).

Effect of Peptide #3 on Cell Proliferation

Figure 3:
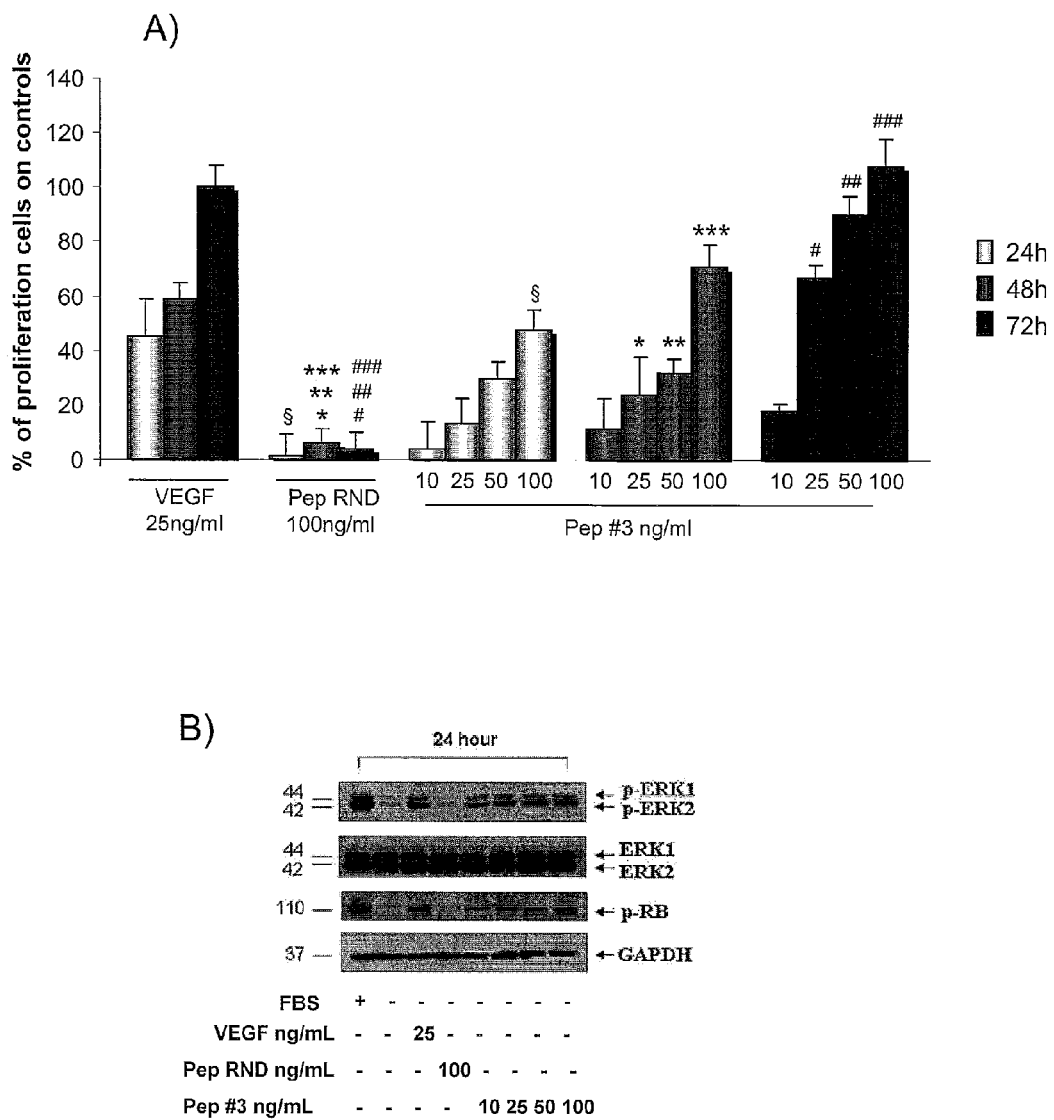
FIG. 3—A) HUVEC cells were incubated in starvation medium (EBM-2, 0.1% heparin, 0.1% BSA) alone or in presence of VEGF165 (25 ng/ml) or with indicated concentrations of Pep #3 or Pep RND (100 ng/ml), for 24, 48 and 72 hours at 37° C. in 5% $CO_2$ atmosphere. Cells were then incubated with CyQUANT® NF reagent for 1 hour at 37° C. and fluorescence intensities of quadruplicate samples were measured with a fluorescence microplate reader using excitation at 485 nm and fluorescence detection at 530 nm. In graph values are calculated as % of proliferating cells compared to controls (untreated cells) at 24, 48 and 72 hours. B) ERK1/2 phosphorylation and phospho-RB was evaluated at 24 hr after stimulation with Pep #3 (10-25-50 and 100 ng/ml), VEGF165 (25 ng/ml) and Pep RND (100 ng/ml). Anti-ERK1/2 and anti-GAPDH antibodies were used as loading control FIG. 4—Angioreactors were prepared and implanted as described in the method section. After 21 days, angioreactors were recovered and photographed using a digital camera (A). In VEGF- and peptide #3-containing angioreactors, new vessel formation was observed. Panel B) Blood vessel development was quantified by fluorescence microscope by determining the number of FITC-lectin-positive cells. 20 fields for sample were analyzed; results are expressed in number of FITC-lectin positive cells/field.
Figure 4:
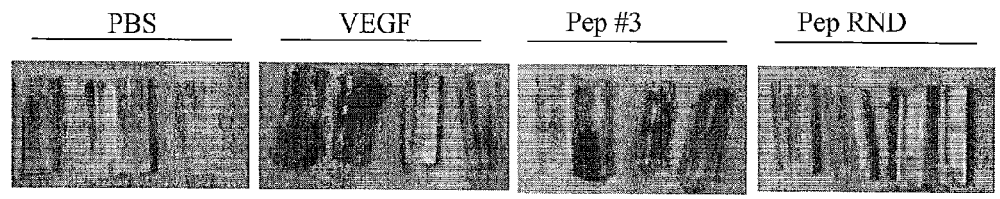
Figure 4:
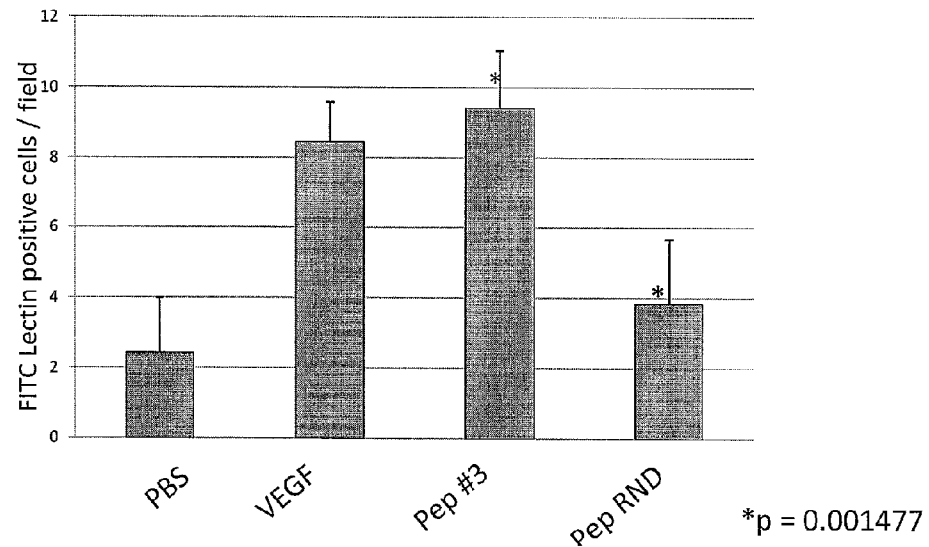

To evaluate whether peptide #3 induces cellular proliferation, a cell proliferation assay was performed on HUVEC cells treated, in serum deprivation conditions, with pep #3 (10-25-50-100 ng/ml) or Pep RND (100 ng/ml). After 24, 48 and 72 hours of treatment cell proliferation was measured by CyQUANT® NF Cell Proliferation Assay Kit. Results obtained from this experiment demonstrated that peptide #3 is able to induce, in a dose dependent manner, cell proliferation in a manner similar to VEGF165 (25 ng/ml) used as positive control. This effect is evident at 24, 48 and 72 hours. Considerable effects were also observed with pep #3 treatment at concentrations of 25 and 50 ng/ml at 48 and 72 hours. The scrambled peptide, pep RND, was ineffective at the concentration of 100 ng/ml. (FIG. 3A).

Moreover, western blot analysis, from whole cells proteins obtain after 24 hours of treatment, confirmed ERK1/2 activation in cells treated with peptide #3 and VEGF165. As a marker of cell proliferation, the RB phosphorylation status was also checked in the same experimental conditions. RB protein, in fact, is able to regulate proliferation by controlling cell cycle progression through the restriction point within the G1 and S phases. Pep #3 and VEGF165 but not Pep RND, enhanced RB phosphorylation, thus indicating cell cycle progression from G1 to S phase (FIG. 3B).

Peptide #3 Pro-Angiogenic Activity In Vivo

Pro-angiogenic peptide #3 activity was also assayed in an in vivo test using DIVAA (Directed in Vivo Angiogenesis Angioreactor). DIVAA test is performed by implanting angioreactors into the dorsal flank of mice; this allows a quantitative assessment of blood vessel development. In FIG. 3A are shown pictures from angioreactors containing PBS (negative control), VEGF (positive control), peptide #3 (100 ng/ml) or scrambled Pep-RND peptide (100 ng/ml), removed after 21 days from subcutaneous implantation in mice. Blood vessels development was observed in VEGF- and peptide #3-containing angioreactors. Indeed, as shown in FIG. 3B, the induction of new vessel formation by peptide #3 was 3.8 fold greater with respect to negative controls (peptide #3 vs Pep-RND: 3.83±0.67, p=0.000835; peptide #3 vs PBS: 2.4±0.42, p=0.001477).

The invention claimed is:

1. A synthetic peptide comprising the amino acid sequence selected from the group consisting of: KQCMWIKPHQGQWTCTS [SEQ ID No 2](cyclic: Cys residues make a disulfide bond) and KQLLWIRSGDRPWYYTS [SEQ ID No 3].

2. A pharmaceutical composition compromising the peptide of claim 1 and appropriate diluents and/or excipients.

* * * * *